United States Patent
Wariar et al.

(10) Patent No.: US 7,147,615 B2
(45) Date of Patent: Dec. 12, 2006

(54) NEEDLE DISLODGEMENT DETECTION

(75) Inventors: Ramesh Wariar, Tampa, FL (US); Thomas P. Hartranft, Clearwater, FL (US); Norm Cameron, St. Petersburg, FL (US); Angel Lasso, Tampa, FL (US); Hector Caro, St. Petersburg, FL (US)

(73) Assignee: Baxter International Inc., Deerfield, IL (US)

(*) Notice: Subject to any disclaimer, the term of this patent is extended or adjusted under 35 U.S.C. 154(b) by 288 days.

(21) Appl. No.: 09/888,154

(22) Filed: Jun. 22, 2001

(65) Prior Publication Data

US 2002/0198483 A1    Dec. 26, 2002

(51) Int. Cl.
*A61M 37/00* (2006.01)
*A61M 1/00* (2006.01)
*A61M 31/00* (2006.01)
*A61B 5/00* (2006.01)
*A61B 5/04* (2006.01)

(52) U.S. Cl. ............... 604/6.16; 604/4.01; 604/31; 604/65; 600/371; 600/384; 600/386; 600/393

(58) Field of Classification Search .............. 128/886, 128/DIG. 26; 604/4.01–6.06, 65–67, 174–180, 604/168.01, 900, 19, 27–29, 31; 600/390, 600/391–395, 371, 547, 437, 459, 462, 464, 600/309, 362, 363, 365, 368–71, 382, 384, 600/386; 340/573.5, 605; 422/44, 68.1, 422/82.01, 82.02, 105, 108, 110, 111; 494/1, 494/10, 36, 37

See application file for complete search history.

(56) References Cited

U.S. PATENT DOCUMENTS

| 2,127,538 | A | * | 8/1938 | Seiger ............... 200/61.05 |
| 3,682,162 | A | | 8/1972 | Colyer |
| 3,731,685 | A | | 5/1973 | Eidus |
| 3,759,261 | A | | 9/1973 | Wang |
| 3,778,570 | A | | 12/1973 | Shuman |
| 3,809,078 | A | | 5/1974 | Mozes |
| 3,810,140 | A | | 5/1974 | Finley |
| 3,814,249 | A | | 6/1974 | Eaton |
| 3,832,067 | A | | 8/1974 | Kopf et al. |
| 3,832,993 | A | | 9/1974 | Clipp |
| 3,882,861 | A | | 5/1975 | Kettering et al. |
| 3,900,396 | A | | 8/1975 | Lamadrid |
| 3,946,731 | A | | 3/1976 | Lichtenstein |
| 4,017,190 | A | | 4/1977 | Fischel |

(Continued)

FOREIGN PATENT DOCUMENTS

DE    28 38 414    3/1980

(Continued)

*Primary Examiner*—Patricia Bianco
(74) *Attorney, Agent, or Firm*—Joseph P. Reagen; Bell, Boyd & Lloyd LLC

(57) ABSTRACT

An apparatus for detecting dislodgement of a needle inserted into a patient includes a sensor for detecting wetness due to blood and a sensor holder to secure the sensor to the patient such that the sensor detects wetness due to blood loss from the patient upon dislodgement of the needle. Methods and apparatuses for detecting, monitoring and/or controlling blood loss from a patient due to needle dislodgement are also provided.

29 Claims, 3 Drawing Sheets

U.S. PATENT DOCUMENTS

| | | | |
|---|---|---|---|
| 4,022,211 A | 5/1977 | Timmons et al. | |
| 4,026,800 A | 5/1977 | Friedrich et al. | |
| 4,055,496 A | 10/1977 | Friedrich et al. | |
| 4,085,047 A | 4/1978 | Thompson | |
| 4,087,185 A | 5/1978 | Lamadrid | |
| 4,162,490 A | 7/1979 | Fu et al. | |
| 4,166,961 A | 9/1979 | Dam et al. | |
| 4,181,610 A | 1/1980 | Shintani et al. | |
| 4,191,950 A | 3/1980 | Levin et al. | |
| 4,192,311 A | 3/1980 | Felfoldi | |
| 4,193,068 A | 3/1980 | Ziccardi | |
| 4,231,366 A | 11/1980 | Schael | |
| 4,231,370 A | 11/1980 | Mroz et al. | |
| 4,327,731 A | 5/1982 | Powell | |
| 4,353,368 A | 10/1982 | Slovak et al. | |
| 4,366,051 A | 12/1982 | Fischel | |
| 4,484,573 A | 11/1984 | Yoo | |
| 4,501,583 A | 2/1985 | Troutner | |
| 4,534,756 A | 8/1985 | Nelson | |
| 4,539,559 A | 9/1985 | Kelly et al. | |
| 4,583,546 A | 4/1986 | Garde | |
| 4,648,869 A | 3/1987 | Bobo, Jr. | |
| 4,655,742 A * | 4/1987 | Vantard | 604/6.05 |
| 4,710,163 A | 12/1987 | Butterfield | |
| 4,739,492 A | 4/1988 | Cochran | |
| 4,796,014 A | 1/1989 | Chia | |
| 4,846,792 A | 7/1989 | Bobo, Jr. et al. | |
| 4,862,146 A | 8/1989 | McCoy et al. | |
| 4,898,587 A | 2/1990 | Mera | |
| 4,931,051 A | 6/1990 | Castello | |
| 4,941,882 A * | 7/1990 | Ward et al. | 604/180 |
| 4,959,060 A | 9/1990 | Shimomura et al. | |
| 4,965,554 A | 10/1990 | Darling | |
| 4,976,698 A | 12/1990 | Stokley | |
| 4,977,906 A | 12/1990 | DiScipio | |
| 4,979,940 A | 12/1990 | Bobo, Jr. et al. | |
| 4,981,467 A | 1/1991 | Bobo, Jr. et al. | |
| 5,036,859 A * | 8/1991 | Brown | 600/547 |
| 5,078,682 A * | 1/1992 | Miki et al. | 604/65 |
| 5,084,026 A | 1/1992 | Shapiro | |
| 5,088,990 A | 2/1992 | Hivale et al. | |
| 5,121,630 A | 6/1992 | Calvin | |
| 5,137,033 A | 8/1992 | Norton | |
| 5,139,482 A | 8/1992 | Simeon et al. | |
| 5,197,958 A | 3/1993 | Howell | |
| 5,247,434 A | 9/1993 | Peterson et al. | |
| 5,264,830 A | 11/1993 | Kline et al. | |
| 5,266,928 A | 11/1993 | Johnson | |
| 5,291,181 A | 3/1994 | DePonte | |
| 5,314,410 A | 5/1994 | Marks | |
| 5,341,127 A | 8/1994 | Smith | |
| 5,354,289 A | 10/1994 | Mitchell et al. | |
| 5,389,093 A | 2/1995 | Howell | |
| 5,392,032 A | 2/1995 | Kline et al. | |
| 5,395,358 A | 3/1995 | Lu | |
| 5,435,010 A | 7/1995 | May | |
| 5,439,442 A | 8/1995 | Bellifemine | |
| 5,468,236 A | 11/1995 | Everhart et al. | |
| 5,469,145 A | 11/1995 | Johnson | |
| 5,486,286 A | 1/1996 | Peterson et al. | |
| 5,487,827 A | 1/1996 | Peterson et al. | |
| 5,522,809 A | 6/1996 | Larsonneur | |
| 5,542,932 A | 8/1996 | Daugherty | |
| 5,557,263 A | 9/1996 | Fisher et al. | |
| 5,568,128 A | 10/1996 | Nair | |
| 5,570,082 A | 10/1996 | Mahgereffeh et al. | |
| 5,579,765 A * | 12/1996 | Cox et al. | 600/307 |
| 5,603,902 A | 2/1997 | Maltais et al. | |
| 5,649,914 A | 7/1997 | Glaug et al. | |
| 5,670,050 A | 9/1997 | Brose et al. | |
| 5,674,390 A | 10/1997 | Matthews et al. | |
| 5,681,298 A | 10/1997 | Brunner et al. | |
| 5,690,610 A | 11/1997 | Ito et al. | |
| 5,690,624 A | 11/1997 | Sasaki et al. | |
| 5,702,376 A | 12/1997 | Glaug et al. | |
| 5,702,377 A | 12/1997 | Collier, IV et al. | |
| 5,744,027 A | 4/1998 | Connell et al. | |
| 5,760,694 A | 6/1998 | Nissim et al. | |
| 5,762,805 A | 6/1998 | Truitt et al. | |
| 5,766,212 A | 6/1998 | Jitoe et al. | |
| 5,790,035 A | 8/1998 | Ho | |
| 5,790,036 A | 8/1998 | Fisher et al. | |
| 5,796,345 A | 8/1998 | Leventis et al. | |
| 5,797,892 A | 8/1998 | Glaug et al. | |
| 5,800,386 A | 9/1998 | Bellifemine | |
| 5,802,814 A | 9/1998 | Sano | |
| 5,817,076 A | 10/1998 | Fard | |
| 5,838,240 A | 11/1998 | Johnson | |
| 5,845,644 A | 12/1998 | Hughes et al. | |
| 5,862,804 A | 1/1999 | Ketchum | |
| 5,868,723 A | 2/1999 | Al-Sabah | |
| 5,885,264 A | 3/1999 | Matsushita | |
| 5,900,817 A | 5/1999 | Olmassakian | |
| 5,903,222 A | 5/1999 | Kawarizadeh et al. | |
| 5,904,671 A | 5/1999 | Navot et al. | |
| 5,908,411 A | 6/1999 | Matsunari | |
| 5,941,248 A | 8/1999 | Wheeler | |
| 5,947,910 A * | 9/1999 | Zimmet | 600/547 |
| 5,947,943 A | 9/1999 | Lee | |
| 5,959,535 A | 9/1999 | Remsburg | |
| 6,038,914 A | 3/2000 | Carr et al. | |
| 6,063,042 A | 5/2000 | Navot et al. | |
| 6,075,178 A | 6/2000 | La Wilhelm et al. | |
| 6,077,443 A | 6/2000 | Goldau | |
| 6,090,048 A | 7/2000 | Hertz et al. | |
| 6,093,869 A | 7/2000 | Roe et al. | |
| 6,097,297 A | 8/2000 | Ford | |
| 6,113,577 A | 9/2000 | Hakky | |
| 6,149,636 A | 11/2000 | Roe et al. | |
| 6,160,198 A | 12/2000 | Roe et al. | |
| 6,166,639 A | 12/2000 | Pierce et al. | |
| 6,169,225 B1 | 1/2001 | Otsubo | |
| 6,171,289 B1 | 1/2001 | Millot et al. | |
| 6,200,250 B1 | 3/2001 | Janszen | |
| 6,332,874 B1 * | 12/2001 | Eliasen et al. | 604/174 |
| 6,425,878 B1 * | 7/2002 | Shekalim | 604/65 |
| 6,445,304 B1 * | 9/2002 | Bandeian et al. | 340/604 |
| 6,751,500 B1 * | 6/2004 | Hirschman | 600/547 |
| 2003/0128125 A1 * | 7/2003 | Burbank et al. | 340/605 |

FOREIGN PATENT DOCUMENTS

| | | |
|---|---|---|
| DE | 29 48 768 | 6/1981 |
| DE | 30 45 514 | 7/1982 |
| DE | 32 23 086 | 7/1983 |
| DE | 34 40 584 | 5/1986 |
| DE | 3911812 A1 | 4/1989 |
| DE | 38 23 859 | 1/1990 |
| DE | 38 36 712 | 5/1990 |
| DE | 40 00 961 | 7/1991 |
| DE | 40 14 572 | 11/1991 |
| DE | 40 18 953 | 1/1992 |
| DE | 42 39 937 | 8/1995 |
| DE | 19953068 A1 | 11/1999 |
| DE | 19 90 1078 | 2/2000 |
| EP | 270 048 | 6/1988 |
| EP | 328 162 | 5/1989 |
| EP | 328 163 | 5/1989 |
| EP | 332 330 | 2/1993 |
| EP | 895 787 | 2/1999 |
| EP | 611 228 | 4/1999 |
| FR | 2 680 678 | 3/1993 |
| GB | 2145859 | 4/1985 |
| GB | 2177247 | 6/1987 |

| | | | | | | |
|---|---|---|---|---|---|---|
| GB | 2250121 | 5/1992 | | WO | WO 99/12588 | 3/1999 |
| JP | 4008361 | 1/1992 | | WO | WO 99/24145 * | 5/1999 |
| JP | 6178789 | 6/1994 | | WO | WO 99/26686 | 6/1999 |
| JP | 10211278 | 8/1998 | | WO | WO 99/29356 | 6/1999 |
| JP | 11-104233 | * 4/1999 | ................. 210/85 | WO | WO 99/42151 | 8/1999 |
| JP | 11299889 | 11/1999 | | WO | WO 01/06975 | 2/2001 |
| WO | WO 86/04710 | 8/1986 | | WO | WO 01/08729 A1 | 2/2001 |
| WO | WO 94/02918 | 2/1994 | | WO | WO 01/24854 | 4/2001 |
| WO | WO 94/07224 | 3/1994 | | WO | WO 01/68163 A2 | 9/2001 |
| WO | WO 96/25904 | 8/1996 | | | | |
| WO | WO 97/10013 | 3/1997 | | \* cited by examiner | | |

NEEDLE DISLODGEMENT DETECTION

BACKGROUND OF THE INVENTION

The present invention relates generally to medical treatments. More specifically, the present invention relates to the detection of needle dislodgement during medical treatments or therapies, such as hemodialysis.

A variety of different medical treatments relate to removing blood from a patient. For example, hemodialysis treatment utilizes the patient's blood to remove waste, toxins and excess water from the patient. The patient is connected to a hemodialysis machine, and the patient's blood is pumped through the machine. Waste, toxins and excess water are removed from the patient's blood, and the blood is infused back into the patient. Needles are inserted into the patient's vascular access, such as arteries and veins, to transfer the patient's blood to and from the hemodialysis machine. Hemodialysis treatments can last several hours and are generally performed in a treatment center about three to four times per week.

During hemodialysis treatment, dislodgement of the needle inserted into the patient's vascular access, such as veins, can occur. If not detected immediately, this can produce a significant amount of blood loss to the hemodialysis patient. Two important criteria for detecting needle dislodgement are high sensitivity and specificity of the detection method with respect to needle dropout. This can ensure and facilitate a fast response time in order to minimize blood loss due to dislodgement.

Typically, patients undergoing hemodialysis are visually monitored in order to detect needle dislodgement. However, the needle may not be in plain view of the patient or medical staff such that it could delay responsive actions to dislodgement, such as stopping the blood pump of the hemodialysis machine.

Although devices which employ sensors are available and known for detecting a variety of different bodily fluids, these devices may not be suitably adapted to detect needle dislodgement. For example, known devices employing such sensors have been utilized to detect bedwetting and diaper wetness. However, these types of wetness detection devices may not provide an adequate level of sensitivity if applied to detecting blood loss from the patient due to needle dislodgement.

In this regard, the known wetness detection devices may not be able to detect needle drop out with sufficient enough sensitivity and specificity to ensure and facilitate a proper and fast response. Further, as applied to hemodialysis, known wetness detection devices may not be configured to be controllably interfaced, or at least not properly interfaced, with, for example, a hemodialysis machine such that responsive measure can be taken to minimize blood flow due to needle dislodgement once detected. In addition, a number of known wetness detectors are not reusable, or at least must be cleaned after each use, due to the fact that the sensor component contacts fluid when detecting same. This can require extensive cleaning of the sensor, particularly if it has contacted blood, in order to minimize the risk of infection prior to reuse.

Accordingly, efforts have been directed at designing devices for detecting needle dislodgement wherein detection is sensitive and specific to needle drop out or dislodgement such that responsive measures can be suitably taken to minimize blood loss from the patient due to needle dislodgement.

SUMMARY OF THE INVENTION

The present invention provides improved apparatuses and methods for detecting needle dislodgement. In this regard, the present invention provides improved apparatuses that employ a sensor capable of detecting wetness due to blood loss from a patient resulting from needle dislodgement.

To this end, in an embodiment of the present invention, an apparatus for detecting dislodgement of a needle inserted into a patient is provided comprising a sensor capable of detecting wetness due to blood and a sensor holder adapted to secure the sensor in juxtaposition to the needle such that the sensor detects wetness due to blood loss from the patient upon dislodgement of the needle.

In an embodiment, the sensor comprises a resistive sensor, a capacitive sensor or combination thereof.

In an embodiment, the resistive sensor comprises a loop configuration of conductive electrodes.

In an embodiment, the loop configuration includes at least two loops of conductive electrodes.

In an embodiment, the capacitive sensor includes one or more electrodes.

In an embodiment, the capacitive sensor is located within the sensor holder such that the sensor does not contact blood upon detection thereof.

In an embodiment, the sensor produces a signal upon detection of blood loss.

In an embodiment, the apparatus further includes a control device adapted to receive the signal for monitoring and controlling blood loss due to dislodgement of the needle during hemodialysis.

In an embodiment, the control device is attached to the patient.

In an embodiment, the needle includes a venous needle.

In another embodiment of the present invention, an apparatus for detecting needle dislodgement during hemodialysis is provided comprising a sensor holder having a cavity; and a capacitive sensor including an electrode enclosed within the cavity of the sensor holder such that the capacitive sensor is capable of detecting wetness from blood due to needle dislodgement during hemodialysis wherein the capacitive sensor does not contact blood upon detection thereof.

In an embodiment, the electrode includes a single plate electrode.

In an embodiment, the capacitive sensor detects wetness due to blood loss into a sterile pad overlying a vascular access region of a venous needle.

In an embodiment, the sensor holder includes a flexible material that adaptedly conforms to the vascular access region such that the capacitive sensor is capable of detecting blood loss due to needle dislodgement.

In another embodiment of the present invention, an apparatus for detecting dislodgement of a needle inserted into a patient during hemodialysis comprising a resistive sensor capable of detecting wetness due to blood wherein the resistive sensor includes at least two electrodes; and a sensor holder defining an interior for receiving at least a portion of the needle and coupling the resistive sensor to the patient such that the resistive sensor is capable of detecting blood loss due to dislodgement of the needle.

In an embodiment, the pair of electrodes each comprise a loop configuration.

In another embodiment of the present invention, an apparatus for controlling blood loss from a patient during hemodialysis is provided comprising a sensor capable of detecting wetness due to blood and a sensor holder adapted to secure the sensor to the patient such that the sensor produces a signal indicative of wetness due to blood loss from the patient upon dislodgement of a venous needle inserted into the patient. The apparatus further comprises a controller capable of processing the signal to prevent blood flow through the venous needle such that blood loss from the patient due to dislodgement of the venous needle is minimized.

In an embodiment, the sensor holder comprises a pad configuration overlying a vascular access region of the venous needle.

In an embodiment, the apparatus further includes a sterile pad overlying a vascular access region of the venous needle such that the sensor detects wetness in the sterile pad due to blood loss from the patient upon venous needle dislodgement.

In an embodiment, the sensor contacts the sterile pad to detect wetness therein.

In an embodiment, the sensor is located within the sterile pad.

In an embodiment, the controller is in communication with a hemodialysis machine via an electrical communication cable or a cordless interface to minimize blood loss due to venous needle dislodgement.

In an embodiment, the controller is adapted to monitor one or more hemodialysis treatment parameters including wetness due to blood loss, change in blood flow, detection of the arterial air bubbles or combinations thereof.

In an embodiment, the controller comprises a display for monitoring each of the hemodialysis treatment parameters.

In an embodiment, the controller is attached to the patient.

In yet another embodiment of the present invention, a method of detecting needle dislodgement is provided. The method comprises the steps of providing a sensor capable of detecting wetness due to blood; inserting a needle into a patient; and securing the sensor to the patient such that the sensor detects blood on the patient due to dislodgement of the needle.

In a further embodiment of the present invention, a method of controlling blood loss from a patient due to needle dislodgement is provided. The method comprises the steps of providing a sensor capable of detecting wetness due to blood; inserting a needle into the patient; securing the sensor to the patient such that the sensor produces a signal indicative of wetness due to blood loss from the patient upon dislodgement of the needle; and processing the signal to prevent blood flow through the venous needle such that blood loss to the patient due to needle dislodgement is minimized.

In an embodiment, the signal is processed for communicating with a hemodialysis machine to minimize blood loss to the patient due to needle dislodgement.

In an embodiment, the signal is processed to shut-off a blood pump of the hemodialysis machine.

In an embodiment, the signal is processed to activate a venous line clamp for preventing blood flow via the venous needle.

In another embodiment, a method of providing dialysis to a patient is provided. The method includes the steps of providing a sensor capable of detecting wetness due to blood; inserting a venous needle into the patient; securing the sensor in juxtaposition to the venous needle; passing blood through the venous needle via a hemodialysis machine; and detecting blood loss from the patient upon dislodgement of the venous needle.

In an embodiment, blood flow through the venous needle is stopped upon detecting dislodgement of the venous needle such that blood loss from the patient is minimized.

An advantage of the present invention is to provide an improved apparatus for detecting needle dislodgement.

A further advantage of the present invention is to provide an improved method for detecting needle dislodgement.

Still further, an advantage of the present invention is to provide an improved apparatus for detecting needle dislodgement that employs a sensor which is capable of detecting blood loss from the patient upon needle dislodgement.

Yet still further, an advantage of the present invention is to provide an apparatus that employs a sensor which does not contact blood upon detection thereof.

Furthermore, an advantage of the present invention is to provide an improved apparatus and method for monitoring and/or controlling blood loss from a patient due to needle dislodgement.

Another advantage of the present invention is an improved method for hemodialysis that employs a sensor to detect dislodgement of a venous needle such that blood loss due to needle dislodgement is minimized.

Additionally, an advantage of the present invention is to provide an improved apparatus and method for detecting and/or controlling blood loss from a patient due to venous needle dislodgement during hemodialysis.

Another advantage of the present invention is to provide an improved apparatus and method for monitoring and/or controlling one or more hemodialysis treatment parameters to minimize blood loss from a patient due to needle dislodgement.

Additional features and advantages of the present invention will be described in and apparent from the detailed description of the presently preferred embodiments and the figures.

BRIEF DESCRIPTION OF THE FIGURES

FIG. 2A illustrates an embodiment of a resistive sensor. FIG. 2B illustrates an embodiment of a capacitive sensor.

FIG. 3A illustrates a top perspective view. FIG. 3B illustrates an exploded view. FIG. 3C illustrates a side sectional view.

DETAILED DESCRIPTION OF THE INVENTION

The present invention provides apparatuses and methods for detecting needle dislodgement. More specifically, the present invention provides apparatuses and methods that employ a sensor to detect needle dislodgement such that blood loss due to dislodgement can be controllably minimized.

Although in the embodiment set forth below the apparatus is designed for use in hemodialysis, it should be noted that the apparatus can be used in a number of different therapies. In this regard, the apparatus can be used in non-traditional hemodialysis methods. Such methods included, for example, regeneration and continuous flow therapies which may or may not include hemodialysis, for example, continuous flow peritoneal dialysis. Further, although the present invention, in an embodiment, can be utilized in methods providing dialysis for patients having chronic kidney failure or disease, the present invention can be used for acute dialysis needs, for example, in an emergency room setting.

In general, the apparatus for detecting needle dislodgement of the present invention includes a sensor that is capable of detecting wetness due to blood and a sensor holder that can be adapted to secure the sensor to a patient such that the apparatus can effectively detect dislodgement of the needle during treatment or therapy. For example, during hemodialysis, dislodgement of a venous needle can occur. If dislodged, a significant amount of blood loss can occur within a relatively short period of time. In this regard, the sensor of the apparatus of the present invention can detect wetness due to blood loss from the patient resulting from the dislodged needle. The detection of blood loss is an indication that the needle has become dislodged. Thus, needle dislodgement can be detected.

Applicants have surprisingly found that the apparatus of the present invention can detect needle dislodgement, particularly venous needle dislodgement, with high sensitivity and specificity. In this regard, the apparatus of the present invention can be utilized to controllably minimize blood loss from the patient due to the dislodged needle.

It should be appreciated that the apparatus of the present invention can include a variety of different configurations and other components in addition to the sensor and sensor holder depending on the application of the detection apparatus. It should further be appreciated that the various components of the apparatus can include a variety of different and suitably known materials such that needle dislodgement can be effectively and immediately detected to minimize blood loss from the patient due to dislodgement of the needle.

Figure 1:
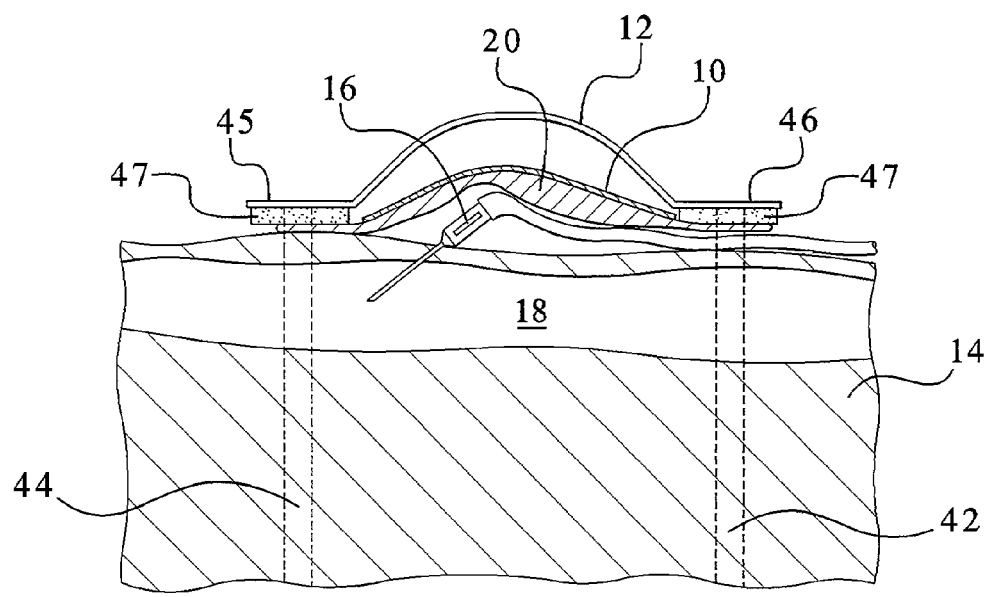
FIG. 1 illustrates a perspective view of an embodiment of an apparatus for detecting needle dislodgement of the present invention.

Referring now to FIG. 1, an embodiment of the present invention includes a sensor 10 and sensor holder 12 that overlies the sensor 10 such that sensor holder 12 secures the sensor 10 to the patient 14 for detecting wetness due to blood loss from the patient 14 upon dislodgement of the needle 16. In an embodiment, the sensor holder 12 includes pad configuration such that it is sized to cover the needle 16 and access region 18 therein.

In an embodiment, the sensor holder 12 includes a rigid material, such as a rigid plastic material, that has a preferable dome shape. In this regard, the sensor holder 12 can act to shield and protect the sensor 10, needle 16 and other components that it covers in addition to properly positioning and securing the sensor 10 over the access or insertion region 18 of the needle 16.

In an embodiment, the apparatus can include a sterile barrier 20 overlying the access region 18 between the sensor 10 and needle 16 as shown in FIG. 1. The sterile barrier 20 or pad can include a variety of different medically sterile materials, such as gauze pads, BAND-AIDS or the like. If a gauze pad or typical absorbent pad is used, the sensor 10 can be positioned to contact the absorbent pad. In this position, the sensor 10 can contact blood that is absorbed by the absorbent pad due to a blood loss from the patient 14. The sensor 10 can then detect the presence of blood in the absorbent pad.

The present invention can include a variety of different types and numbers of sensors to detect the presence of blood. In this regard, it should be appreciated that the sensor or sensors can be utilized to detect one or more parameters that are characteristic of blood or blood loss due to needle dislodgement, such as, temperature, color, conductivity, resistance, capacitance, moisture, wetness, the like or combinations thereof.

Figure 2A:
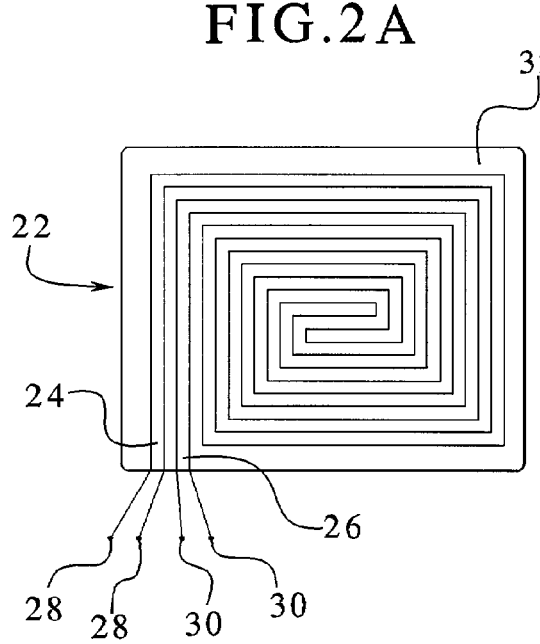
FIGS. 2A and 2B illustrate an embodiment of a sensor of the present invention.

In an embodiment, a resistive sensor 22 can be effectively utilized to detect the presence wetness in the absorbent pad due to blood. The resistive sensor 22 is capable of measuring the change in conductivity of the gauze which results from blood loss or leakage. The resistive sensor 22 can be configured in a variety of different and suitably known ways. Preferably, the resistive sensor 22 includes a looped configuration of electrodes. More preferably, the conductive electrodes 24,26 are configured in the form of two loops as shown in FIG. 2A.

Having this two loop configuration, the electrical continuity of the sensor 22 can be readily and easily tested to monitor and ensure that the sensor 22 is properly functioning. In this regard, each conductive loop 24,26 can be individually tested for short circuiting by attaching a typical electronic testing device to the contact ends 28,30 of each of the conductive loops 24,26. The loop configuration may also provide a higher level of sensitivity with respect to detecting blood as compared to conventional electrode configurations, such as typical electrode pairs that are essentially straight in length extending parallel to each other.

The conductive electrodes 24,26 of the resistive sensor 22 are generally attached to a substrate 32. Typically, the substrate 32 is a dielectric material, such as a plastic film or other like material. The conductive electrode material can be any suitably known conductive material. It should be appreciated that the conductive sensor can be excited by an AC or DC current source wherein the voltage drop between the two conductive electrode loops is used to measure the change in conductivity as a result of the pad or absorbent pad being wetted by blood.

Figure 2B:
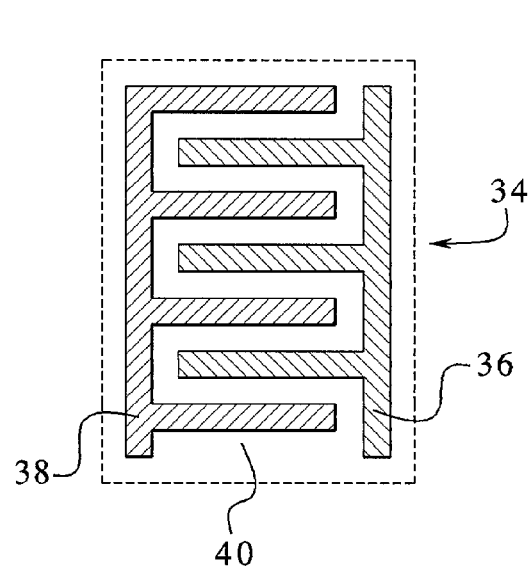

In an embodiment, a capacitive sensor 34 can be used in place of or in addition to the resistive sensor 22. In an embodiment, the sensor 34 can include one or more electrodes for detection purposes. As illustrated in FIG. 2B, the capacitive sensor 34 includes two electrodes 36,38 each made from a known copper material. The electrodes 36,38 can be arranged in any suitable fashion, preferably in an interwoven configuration as shown in FIG. 2B. In this regard, a change in the capacitance between the electrodes 36,38 can be effectively measured and/or monitored for detecting the presence of blood in the absorbent pad. The electrodes are typically attached to a substrate 40 of a suitably known material.

It should be appreciated that in both of the resistive and capacitive sensors the output voltage of the sensor will be compared against a preset voltage to determine whether the absorbent pad is wet or dry. The rate of change of the output voltage may also be used to discriminate a blood loss event from noise, such as drift in the sensor output or wetness due to patient's sweat.

It should be appreciated that the sensor holder 12 can be secured to the patient 14 in a variety of suitable and known ways to ensure that the sensor 10 is properly secured and positioned over the insertion region 18 of the needle. In an embodiment, the sensor holder 12 can be secured to the patient 14 by a fastener, for example, having one or more straps as shown in FIG. 1. For example, a strap 42,44 can be used to fasten a separate end 45,46 of the pad of the sensor holder 12. The straps 42,44 can include any variety of different materials, such as elastic, rigid or the like depending on the application. The straps 42,44 can be fastened to the sensor holder 12 by any known fastening mechanisms, such as a hoop and loop fastener, a buckle fastener, a Velcro fastener or other like fasteners.

In an embodiment, the apparatus can also include a force transducer 47, such as a pressure or motion sensitive transducer, to measure and monitor the force upon which the sensor holder is secured to the patient 14. The force transducer 47 can be utilized to ensure that the applied force is suitable for the particular application. In addition, the force transducer 47 may be adapted to enable one to monitor, control and adjust the applied force as deemed appropriate.

Figure 3A:
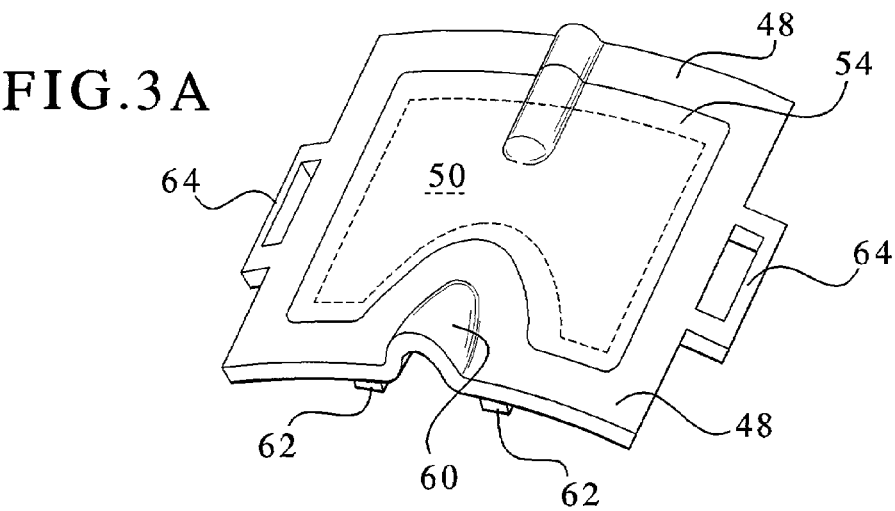
FIGS. 3A to 3C illustrate an embodiment of an apparatus for detecting needle dislodgement of the present invention showing a sensor holder and a sensor located inside of the sensor holder.
Figure 3B:
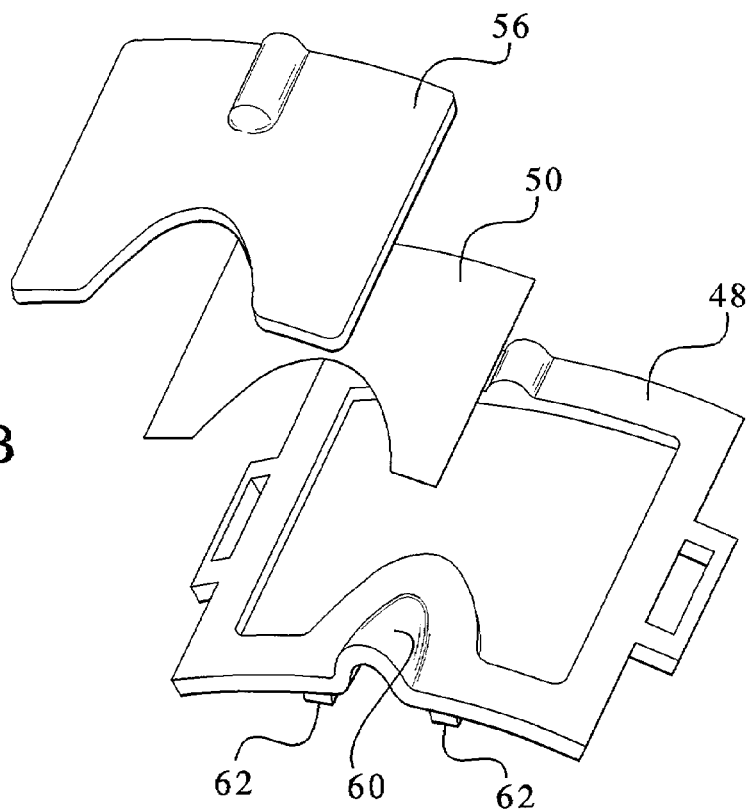
Figure 3C:
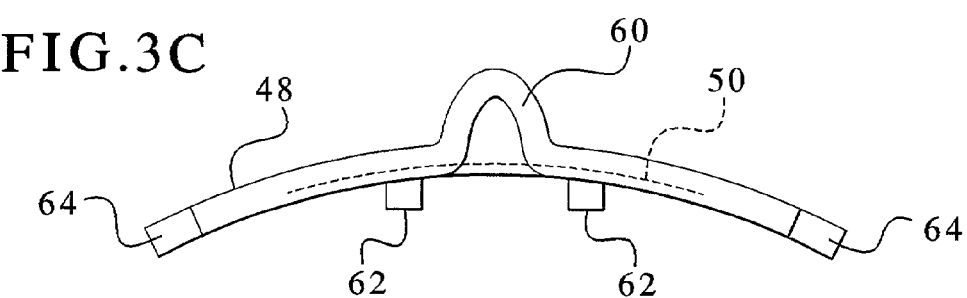

As previously discussed, the apparatus can be configured in a variety of different and suitable known ways to properly secure the sensor to the patient and to securely hold the needle in place to prevent dislodgement. In an embodiment, the apparatus can include a sensor holder 48 and a sensor 50 that is contained or located within the sensor holder 48 as shown in FIGS. 3A to 3C. In general, the sensor holder 48 is made of a suitable type of material, preferably a material that is impermeable to fluids, such as a plastic-based material. In this way, blood due to blood loss from the patient upon dislodgement of the needle does not contact the sensor. Even so, the sensor 50 is still capable of detecting the presence of blood. In this regard, the sensor 50 can be used repeatedly without having to clean it after each use, or at least minimizing the amount of cleaning that is required.

In an embodiment, the sensor holder 48 includes a base 52 with a cavity 54 for holding the sensor 50 inside of the sensor holder 48 as shown in FIGS. 3A to 3C. The sensor holder 48 further includes a lid or top 56 to cover the sensor 50 once inside of the cavity 54. Preferably, the sensor is inserted into the cavity and the cavity is over-molded in a known and suitable way. Alternatively, the lid 56 can be removably attached.

The sensor holder 48 is preferably made from a molded flexible plastic or polymeric material for protecting and securing the sensor, needle and other components of the apparatus of the present invention as previously discussed. It also has a preferable angular shape such that the sensor holder 48 effectively covers the vascular access region of the needle which can be located on any suitable part of the patient's body, such as the upper arm, lower arm, upper thigh area or the like. This also facilitates securing the sensor holder to the patient and can further enhance the comfort level of the patient during use.

It should be appreciated that the sensor holder can be made from a variety of different and suitable materials and configured in a variety of different ways. For example, the thickness of the sensor holder is such that it does not compromise the integrity of the sensor holder to protect the needle and properly hold the sensor while at the same time it does not compromise the extent to which the sensor is capable of detecting blood loss due to needle dislodgement with high sensitivity and selectivity. Further, the sensor holder can be made of a plastic or other like suitable polymeric material that is both flexible and essentially impermeable to liquid of fluid, such as blood. This allows the apparatus to be reused without having to clean the sensor. In this regard, the risk of infection due to reuse can be effectively eliminated or at the very least greatly minimized.

As shown in FIGS. 3A to 3C, the sensor holder 48 has a channeled area 60 under which the needle, respective blood lines and the like are positioned. In addition, the sensor holder 48 can include a pair of spacers 62 that extend along at least a portion of the bottom surface of the sensor holder 48. The channeled area 60 and spacer 62 can act as a guide to further position the needle, blood lines, absorbent pad and the like, such that the sensor 50 is properly aligned with respect to the needle and access region. This can facilitate the detection of blood due to blood loss upon dislodgement of the needle. In this regard, the sensor 50 can be securely positioned in close proximity to the needle without disrupting the way in which the needle is inserted into the patient.

In an embodiment, the sensor 50 preferably includes a capacitive sensor that includes a single electrode formed in a sheet or plate configuration. The electrode is preferably made of copper. As the capacitance of the absorbent pad increases due to the presence of blood, the single electrode capacitive sensor can detect the increased capacitance of blood as compared to air (i.e., no blood present) due to the coupling of field lines between the electrode and the ground of the sensor. The non-contact nature of this type of sensor is desirable because cleaning of the sensor after use can be effectively minimized or avoided as previously discussed.

Applicants have surprisingly found that the capacitive sensor can detect wetness due to the presence of blood, for example, in an absorbent pad overlying the needle, with a high degree of sensitivity and specificity to needle dislodgement without contacting the absorbent pad and for that matter blood. In this regard, the sensor is capable of detecting an increased capacitance of the blood-wetted absorbent pad which results from its large dielectric constant as compared to a dry absorbent pad. This can be done by measuring the charging and discharging times of the electrode or by measuring the change in the dielectric constant due to the presence of blood in other known and suitable ways.

It should be appreciated that an embodiment of the apparatus as shown in FIGS. 3A to 3C can be secured to the patient in a number of different and suitably known ways. In an embodiment, the sensor holder 48 includes a pair of fastener members 64 onto which straps or other like fasteners can be attached to fasten the apparatus to the patient. The straps and/or fasteners can include any suitably known straps and/or fasteners as discussed above.

As previously discussed, the apparatus of the present invention can be effectively utilized to detect needle dislodgement by detecting the presence of wetness due to blood loss upon dislodgement of the needle from the patient. The apparatus can be applied in a number of different applications, such as medical therapies or treatments, particularly hemodialysis. In hemodialysis, needles are inserted into a patient's arteries and veins to connect blood flow to and from the hemodialysis machine.

Under these circumstances, if the needle becomes dislodged, particularly the venous needle (i.e., a needle inserted into a vein), the amount of blood loss from the patient can be significant and immediate. In this regard, the needle dislodgement detection apparatus of the present invention can be utilized to controllably and effectively minimize blood loss from a patient due to dislodgement of the needle, such as during hemodialysis.

Figure 4:
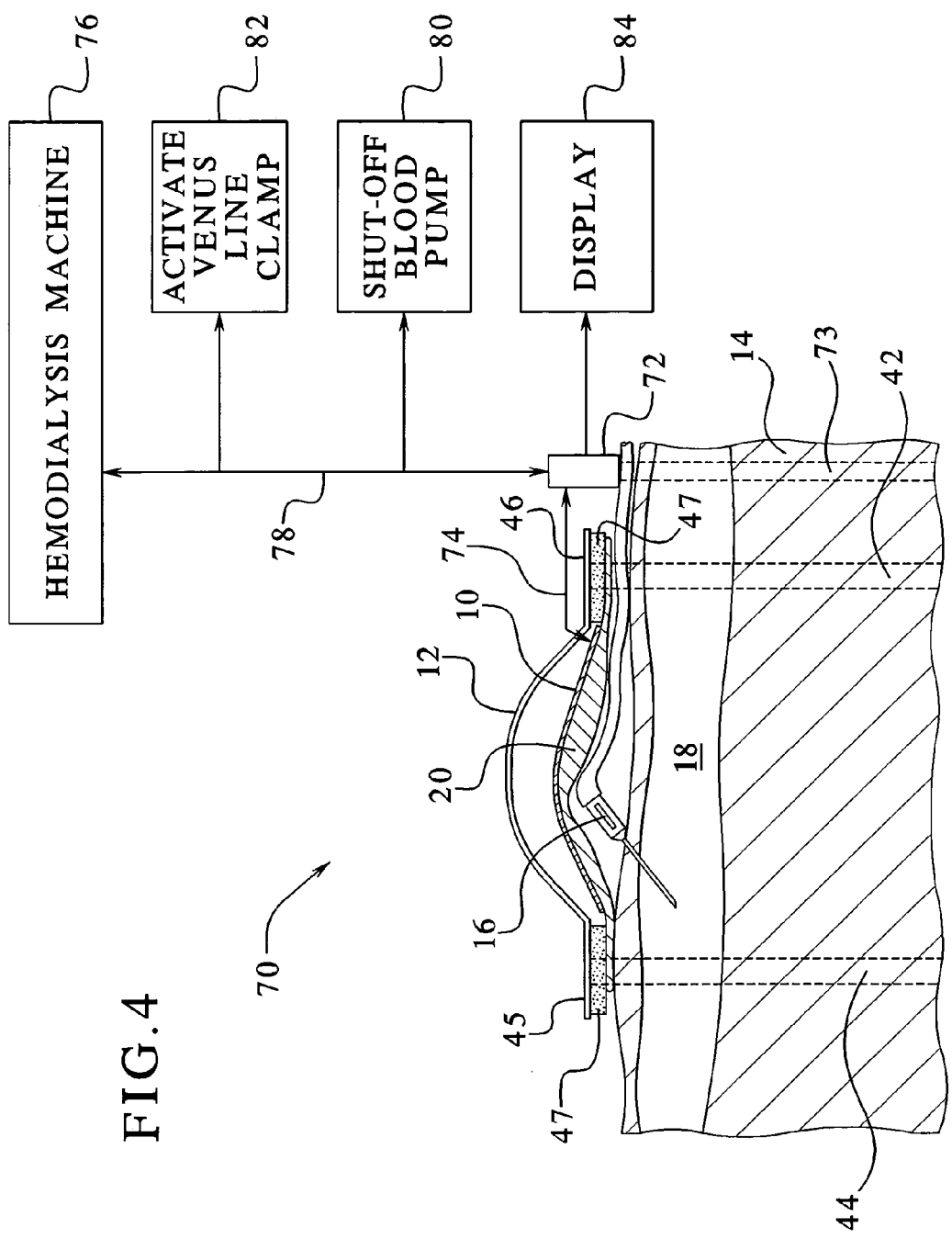
FIG. 4 illustrates an embodiment of an apparatus for detecting needle dislodgement of the present invention.

In an embodiment, the present invention provides an apparatus 70 for controlling the blood loss from a patient due to venous needle dislodgement shown in FIG. 4. The apparatus can include a needle dislodgement device as previously discussed and shown in FIGS. 1 and 4.

In an embodiment, the apparatus 70 includes a controller 72 that is in electrical contact with the sensor 10. The controller 72 can be attached to the patient via an attachment 73 in any suitable way. The controller 72 can be configured in a variety of different ways depending on the application thereof. Upon detection of the presence of blood due to needle dislodgement, the sensor 10 produces a signal indicative of the degree of wetness due to blood. This signal can then be transmitted to the controller 72 which is electrically connected to the sensor 10 via a connection 74 in any suitable way.

The controller 72 can process the signal in a variety of different ways such that the blood loss from the patient is minimized. In an embodiment, the controller 72 is in communication with a hemodialysis machine 76 via a communication connection 78. This communication connection 78 can be either hard wired (i.e., electrical communication cable), a wireless communication (i.e., wireless RF interface), a pneumatic interface or the like. In this regard, the controller 72 can process the signal to communicate with the hemodialysis machine to shut off or stop the blood pump as indicated in box 80—associated with the hemodialysis machine 76 and thus effectively minimize the amount of blood loss from the patient due to needle dislodgement during hemodialysis.

The controller 72 can communicate with the hemodialysis machine in a variety of other ways. For example, the controller 72 and hemodialysis machine can communicate to activate a venous line clamp as shown in box 82 for preventing further blood flow via the venous needle thus minimizing blood loss to the patient. In an embodiment, the venous line clamp is activated by the controller and attached to or positioned in proximity to the sensor and sensor holder such that it can clamp off the venous line in close proximity to the needle. Once clamped, the hemodialysis machine is capable of sensing an increase in pressure and can be programmed to shut-off the blood pump upon sensing pressure within the blood flow line which is above a predetermined level. In this regard, the sensor, sensor holder and venous line clamp can act together as a stand-alone control unit. Alternatively, the venous line clamp can be controllably attached to the hemodialysis machine.

It should be appreciated that the sensor output signal can be combined with other less sensitive blood loss detection methods, such as venous pressure measurements, systemic blood pressure, the like or combinations thereof, to improve specificity to needle dislodgement.

Applicants have found that the apparatus of the present invention can detect blood loss due to needle dislodgement with high sensitivity and selectivity such that responsive measures can be taken to minimize blood loss due to needle dislodgement. The ability to act responsively and quickly to minimize blood loss upon detection thereof is particularly important with respect to needle dislodgement during hemodialysis. If not detected and responded to immediately, the amount of blood loss can be significant. In an embodiment, the present invention is capable of taking active or responsive measures, to minimize blood loss (i.e., shut-off blood pump, activate venous line clamp or the like) within about three seconds or less, preferably within about two to about three second upon detection of needle dislodgement.

In addition, the controller can be utilized to monitor and/or control one or more treatment parameters during hemodialysis. These parameters can include, for example, the detection of blood due to blood loss upon needle dislodgement, the change in blood flow, the detection of air bubbles in the arterial line, detection of movement of the sensor during treatment, detection and/or monitoring of electrical continuity of the sensor or other like treatment parameters. In an embodiment, the controller includes a display 84 for monitoring one or more of the parameters as shown in FIG. 4.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the impending claims.

The invention claimed is:

1. An apparatus for detecting dislodgement of a needle inserted into a patient comprising:
   a sensor having a capacitive sensor, the capacitive sensor configured to detect wetness due to blood; and
   a barrier pad capable of absorbing blood lost from the patient due to the dislodgment of the needle; and
   a sensor holder configured to secure the sensor and the barrier pad adjacent to the needle, wherein the sensor holder secures the barrier pad between the sensor and the needle such that the sensor detects blood absorbed within the barrier pad.

2. The apparatus of claim 1 wherein the capacitive sensor includes one or more electrodes.

3. The apparatus of claim 1 wherein the capacitive sensor is located within the sensor holder such that the sensor detects wetness due to blood loss in the barrier pad.

4. The apparatus of claim 1 wherein the sensor produces a signal upon detection of blood loss.

5. The apparatus of claim 4 further comprising a control device adapted to receive the signal for monitoring and controlling blood loss due to the dislodgement of the needle during hemodialysis.

6. The apparatus of claim 5 wherein the control device is attached to the patient.

7. The apparatus of claim 1 wherein the needle comprises a venous needle.

8. An apparatus for detecting needle dislodgement during hemodialysis comprising:
   a sensor holder having a cavity;
   a barrier pad configured to absorb blood lost from the patient due to the dislodgment of the needle; and
   a capacitive sensor comprising an electrode enclosed within the cavity of the sensor holder such that the capacitive sensor is positioned to detect wetness absorbed within the barrier pad from blood due to needle dislodgement during hemodialysis such that the capacitive sensor detects blood absorbed within the barrier pad.

9. The apparatus of claim 8 wherein the electrode comprises a single plate electrode.

10. The apparatus of claim 8 wherein the barrier pad overlies a vascular access region of a venous needle.

11. The apparatus of claim 10 wherein the sensor holder comprises a flexible material that adaptably conforms to the vascular access region such that the capacitive sensor is capable of detecting blood loss due to needle dislodgement.

12. An apparatus for controlling blood loss from a patient during hemodialysis comprising:
   a barrier pad configured to absorb blood lost from the patient due to the dislodgment of the needle;
   a capacitive sensor configured to detect wetness due to blood;
   a sensor holder configured to secure the sensor and the barrier pad adjacent to the patient such that the sensor produces a signal indicative of wetness detected within the barrier due to blood loss from the patient upon dislodgement of a venous needle inserted into the patient wherein the capacitive sensor detects blood absorbed within the barrier pad; and a controller capable of processing the signal to prevent blood flow through the venous needle such that blood loss from the patient due to dislodgement of the venous needle is minimized.

13. The apparatus of claim 12 wherein the sensor holder comprises a pad configuration overlying an access region of the venous needle.

14. The apparatus of claim 12 wherein the barrier pad overlies an access region of the venous needle.

15. The apparatus of claim 14 wherein the sensor detects a change in a dielectric constant of the barrier pad.

16. The apparatus of claim 14 wherein the sensor is located inside of the sensor holder such that the sensor does not contact the sterile pad upon detecting wetness therein.

17. The apparatus of claim 12 wherein the controller is in communication with a hemodialysis machine via an electrical communication cable or a cordless interface to minimize blood loss due to venous needle dislodgement.

18. The apparatus of claim 17 wherein the controller is adapted to monitor one or more hemodialysis treatment parameters including wetness due to blood loss, change in blood flow and detection of arterial air bubbles during hemodialysis.

19. The apparatus of claim 18 wherein the controller is attached to the patient for electrical connection to the sensor.

20. The apparatus of claim 18 wherein the controller comprises a display for monitoring each of the parameters.

21. A method of detecting needle dislodgement comprising the steps of:
providing a barrier pad to absorb blood lost from the patient due to the dislodgment of the needle; and
providing a capacitive sensor configured to detect wetness due to blood wherein the sensor detects blood absorbed within the barrier pad;
inserting a needle into a patient; and
securing the sensor and the barrier pad to the patient such that the sensor detects blood absorbed within the barrier pad on the patient upon dislodgement of the needle.

22. The method of claim 21 wherein the needle comprises a venous needle inserted into the patient for hemodialysis.

23. A method of controlling blood loss from a patient due to needle dislodgement comprising the steps of:
providing a capacitive sensor configured to detect wetness due to blood;
providing a barrier pad to absorb blood lost from the patient due to the dislodgment of the needle; and
inserting a needle into the patient;
securing the sensor and the barrier pad adjacent to the patient such that the sensor produces a signal indicative of wetness within the barrier pad due to blood loss from the patient upon dislodgement of the needle and detects blood absorbed within the barrier pad; and
processing the signal to prevent blood flow through the venous needle such that blood loss from the patient due to needle dislodgement is minimized.

24. The method of claim 23 wherein the needle comprises a venous needle inserted into the patient for hemodialysis.

25. The method of claim 24 wherein the signal is processed for communicating with a hemodialysis machine to minimize blood loss to the patient due to needle dislodgement.

26. The method of claim 25 wherein the signal is processed to shut-off a blood pump of the hemodialysis machine.

27. The method of claim 25 wherein the signal is processed to activate a venous line clamp for preventing blood flow via the venous needle.

28. A method of providing dialysis to a patient comprising the steps of:
providing a barrier pad;
providing a capacitive sensor to detect wetness due to blood wherein the sensor does not contact blood upon detection thereof;
inserting a venous needle into the patient;
securing the sensor and the barrier pad in juxtaposition to the venous needle;
passing blood through the venous needle via a hemodialysis machine; and
detecting wetness within the barrier pad indicative of blood loss from the patient upon dislodgement of the venous needle such that the sensor detects blood absorbed within the barrier pad.

29. The method of claim 28 wherein blood flow through the venous needle is stopped upon detecting dislodgement of the venous needle such that blood loss from the patient is minimized.

* * * * *